United States Patent
Rahman et al.

(10) Patent No.: US 10,241,139 B2
(45) Date of Patent: Mar. 26, 2019

(54) MOBILITY PLATFORM BASED NON-CONTACT VOLTAGE DETECTOR

(71) Applicant: Honeywell International Inc., Morris Plains, NJ (US)

(72) Inventors: Ataur Rahman, Hyderabad (IN); Nagaraju Rachakonda, Hyderabad (IN); Ravi Kumar Avupati, Hyderabad (IN); Antonio Vitucci, Wauconda, IL (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 15/575,554

(22) PCT Filed: Jun. 2, 2015

(86) PCT No.: PCT/US2015/033676
§ 371 (c)(1),
(2) Date: Nov. 20, 2017

(87) PCT Pub. No.: WO2016/195660
PCT Pub. Date: Dec. 8, 2016

(65) Prior Publication Data
US 2018/0136262 A1  May 17, 2018

(51) Int. Cl.
*H04M 1/00* (2006.01)
*G01R 19/155* (2006.01)
(Continued)

(52) U.S. Cl.
CPC ........ *G01R 19/155* (2013.01); *A61N 1/3787* (2013.01); *G01R 21/08* (2013.01);
(Continued)

(58) Field of Classification Search
CPC ........ G01R 31/40; G01R 21/08; H04B 3/544; H02J 7/007; H02J 7/025; A61N 1/3787
(Continued)

(56) References Cited

U.S. PATENT DOCUMENTS

| 8,275,413 B1 | 9/2012 | Fraden et al. |
| 2008/0079436 A1 | 4/2008 | Gollhardt et al. |

(Continued)

FOREIGN PATENT DOCUMENTS

| CN | 204350107 U | 5/2015 |
| WO | 2016195660 A1 | 12/2016 |

OTHER PUBLICATIONS

PCT Application No. PCT/US2015/033676, International Search Report, dated Aug. 24, 2016, 6 pages.
(Continued)

*Primary Examiner* — John A Tweel, Jr.
*Assistant Examiner* — Munear T Akki
(74) *Attorney, Agent, or Firm* — Craige Thompson; Thompson Patent Law

(57) ABSTRACT

A non-contact voltage detector module pluggable to a mobile communication device. The non-contact voltage comprises an antenna, a connector configured for connecting to a connector of a mobile communication device, and an assembly coupled to the antenna and the connector. The assembly converts an electromagnetic field received by the antenna to an indication of a strength of the electromagnetic field and transmits the indication of the strength of the electromagnetic field via the connector.

19 Claims, 7 Drawing Sheets

(51) Int. Cl.

| | |
|---|---|
| *H04B 3/54* | (2006.01) |
| *G01R 21/08* | (2006.01) |
| *H02J 7/02* | (2016.01) |
| *H02J 7/00* | (2006.01) |
| *A61N 1/378* | (2006.01) |
| *G01R 31/40* | (2014.01) |
| *H04W 4/38* | (2018.01) |
| *H04M 1/21* | (2006.01) |

(52) U.S. Cl.
CPC .............. *G01R 31/40* (2013.01); *H02J 7/007* (2013.01); *H02J 7/025* (2013.01); *H04B 3/544* (2013.01); *H04M 1/21* (2013.01); *H04W 4/38* (2018.02); *H04M 2250/12* (2013.01)

(58) Field of Classification Search
USPC .................. 340/660; 324/72.5; 320/101, 134
See application file for complete search history.

(56) References Cited

U.S. PATENT DOCUMENTS

| | | |
|---|---|---|
| 2009/0033336 A1 | 2/2009 | Blanchard |
| 2011/0184679 A1 | 7/2011 | Kalokitis |
| 2014/0164228 A1 | 6/2014 | Pathak |
| 2015/0028801 A1* | 1/2015 | Carobolante ............. H02J 7/00 320/108 |

OTHER PUBLICATIONS

PCT Application No. PCT/US2015/033676, Written Opinion of the International Searching Authority, dated Aug. 24, 2016, 9 pages.

* cited by examiner

MOBILITY PLATFORM BASED NON-CONTACT VOLTAGE DETECTOR

CROSS-REFERENCE TO RELATED APPLICATIONS

The present application claims priority to and is the National Stage of International Application No. PCT/US2015/033676 filed on Jun. 2, 2015 by Rahman, et al. and entitled "Mobility Platform Based Non-Contact Voltage Detector" which is incorporated herein by reference in its entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Mobile phones are owned by a high percentage of people. As mobile phone technology advances, more and more functionality is provided to the mobile phones, for example by applications developed by third parties and installed onto the mobile phone. Mobile phones may be viewed, in one perspective, as mobile computing and communicating platforms. Sometimes workers may integrate their mobile phones into their work processes, for example installing third party applications on their phones that provide specialized functionality related to their jobs.

SUMMARY

In an embodiment, a non-contact voltage detector module pluggable to a mobile communication device is disclosed. The non-contact voltage comprises an antenna, a connector configured for connecting to a connector of a mobile communication device, and an assembly coupled to the antenna and the connector. The assembly converts an electromagnetic field received by the antenna to an indication of a strength of the electromagnetic field and transmits the indication of the strength of the electromagnetic field via the connector.

In an embodiment, another non-contact voltage detector module pluggable to a mobile communication device is disclosed. The non-contact voltage detector module comprises an antenna, an analog module coupled to the antenna that amplifies an input from the antenna, filters the amplified antenna input, and rectifies the filtered input, and a processing module coupled to the analog module. The processing module converts the rectified input from an time varying analog value to a sequence of digital values and converts the digital values to a pulse signal restricted to a frequency range of the human voice where the frequency of the pulse signal is determined by the processing module based on the amplitude of the digital values. The non-contact voltage detector module further comprises a signal conditioning module coupled to the processing module that smooths the pulse signal and a connector coupled to the signal conditioning module that outputs the smoothed signal.

In an embodiment, a method of determining that an electrical power line is energized is disclosed. The method comprises receiving a signal by an antenna of a non-contact voltage detector module connected to a mobile phone, where the signal comprises an electromagnetic field radiated by an energized electrical power line, amplifying the received signal by the non-contact voltage detector module, and rectifying the amplified signal by the non-contact voltage detector module. The method further comprises converting the amplified signal to a pulse wave signal by the non-contact voltage detector module, where a frequency of the pulse wave is determined by an amplitude of the amplified signal and smoothing the pulse wave signal by the non-contact voltage detector module to form an alternating current signal comprising a first harmonic frequency that corresponds to the frequency of the pulse wave. The method further comprises outputting the alternating current signal by the non-contact voltage detector module to the mobile phone, processing the alternating current signal by a non-contact voltage detection application executing on the mobile phone to detect an energized state of the electrical power line, and presenting an indication of the energized state of the electrical power line by the mobile communication device.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
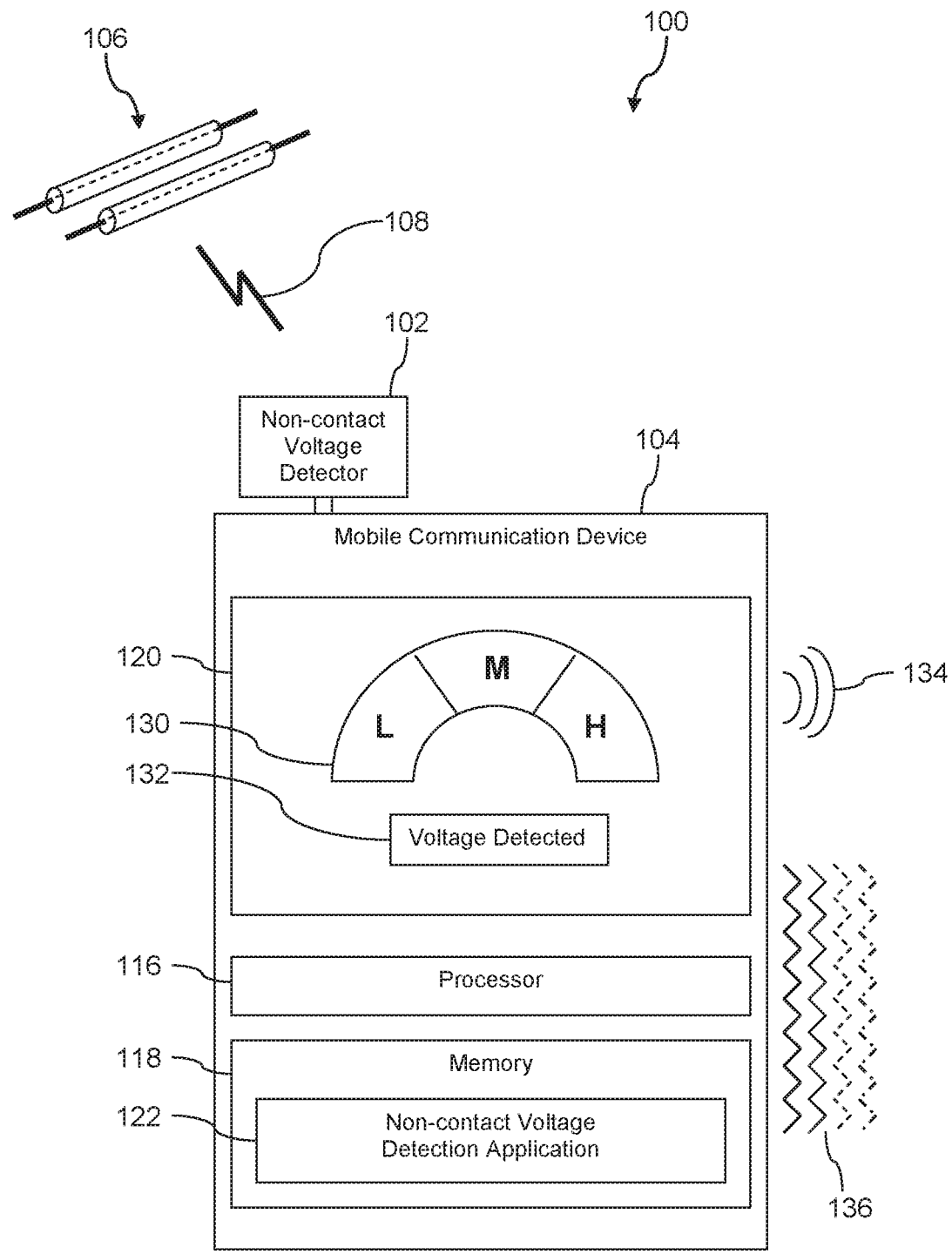
FIG. 1 is an illustration of a non-contact voltage detector system according to an embodiment of the disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The present disclosure teaches a non-contact voltage detector module that plugs into a mobile communication device (e.g., a mobile phone) and a third party application on the mobile communication device that processes input from the module to present an indication of whether an electrical power line is energized or not energized. The detector module comprises an antenna that receives ambient electromagnetic waves radiated by proximate electrical power lines. The received electromagnetic energy is processed by the module, converted by the module to a frequency signal, and transmitted as the frequency signal to the microphone input of the mobile communication device. The application on the mobile communication device processes the frequency signal to determine if the antenna is receiving electromagnetic energy from an energized electrical power line.

When no electromagnetic energy is received by the antenna, the module outputs a frequency signal at a low frequency, e.g., about 1,000 Hz. Outputting a frequency signal even when no electromagnetic energy is received by the module promotes the application on the mobile communication device detecting that the module is plugged in. When the application is first launched on the mobile communication device, if no frequency signal is detected, the application may present a notification to the user to plug in the module and/or to turn on the module. When a strong electromagnetic energy is received by the antenna, the module outputs a frequency signal at a high frequency. The application interprets the input of a frequency signal that is greater in frequency than the low frequency signal to indicate that the proximate electrical power line is energized. A frequency signal input of greater than about 1,500 Hz or a frequency signal input of greater than about 2,000 Hz may be predefined as a threshold for determining that the proximate electrical power line is energized. The application presents one or more indications of the energization of the electrical power line, for example an illumination on a display of the device, a flashing illumination on the display, an aural alert tone from a speaker of the device, and/or a vibration from a vibrator mechanism of the device. The module may further output an indication of a frequency of the electrical power line, for example an indication that the power line carries 60 Hz electrical power or an indication that the power line carries 50 Hz electrical power. In response, the application may present an indication of 50 Hz electrical power or 60 Hz electrical power on the display of the device. The non-contact voltage detector module mated with a mobile phone executing the application may promote safety of employees working with electrical power distribution lines, for example construction or maintenance workers. The user may be able to determine at a distance, in a non-contacting interaction, if electrical power lines are energized or not, thereby allowing the user to avoid an injury that might have resulted when he or she thinks that the electrical power line is not energized when in fact it is energized.

Turning now to FIG. 1, a system 100 is described. In an embodiment, the system 100 comprises a non-contact voltage detector module 102 and a mobile communication device 104. When held proximate to electrical power lines 106 that radiate an electromagnetic field 108, the non-contact voltage detector module 102 may detect the presence of the electromagnetic field 108 and transmit an indication that the lines 106 are energized to the mobile communication device 104. The mobile communication device 104 may be a mobile phone, a smart phone, a personal digital assistant (PDA), a media player, or a wearable computer.

In an embodiment, the mobile communication device 104 comprises a processor 116, a memory 118, a display 120, and a non-contact voltage detection application 122 stored in the memory 118. In some contexts, the non-contact voltage detection application 122 may be referred to as a third party application. The application 122 may be developed by a party unaffiliated with a manufacturer of the mobile communication device 104 and unaffiliated with a wireless communication service provider that provides service to the device 104. A user of the mobile communication device 104 may download and install the application 122 on the mobile communication device 104, for example upon purchasing the non-contact voltage detector module 102. When executed by the processor 116, the application 122 processes a frequency input from the module 102 and may present an indication of voltage and/or electromagnetic energy detected by the module 102.

The indication of voltage is not intended to provide a precise voltage measurement but instead (a) an indication that the power line 106 is energized or is dead and (b) a general sense as to whether the voltage is low voltage, medium voltage, or high voltage. Note that the strength of the electromagnetic field incident on the detector 102 varies with the distance of the detector 102 from the lines 106 proportional to the factor $[1/r^2]$ (said in words, inversely proportional to the square of the distance from the lines 106). For improved results in comparing voltage levels, a user may desirably hold the detector 102 about the same distance from the lines 106 when making different energization determinations, to the extent this is feasible. Additionally, the user must always adhere to best safety practices for maintaining safe distance from high voltage lines.

If a voltage or electromagnetic energy is detected by the module 102, the application 122 may present a variable indication 130 of the amplitude or strength of the voltage or electromagnetic energy detected by the module 102. For example, a low sector of the variable indication 130 may illuminate when a low amplitude is detected, a medium sector of the variable indication 130 may illuminate when a medium amplitude is detected, and a high sector of the variable indication 130 may illuminate when a high amplitude is detected.

It is understood that a variety of different variable indications 130 are contemplated for presentation on the display 120. For example, a needle may be presented that sweeps clockwise over the indication 130 as the detected amplitude increases. Additionally, a voltage detected message 132 may be presented by the application 122 on the display 120. The application 122 may cause the message 132 to flash when the voltage or electromagnetic field is detected. The application 122 may cause the message 132 to flash more rapidly for higher detected amplitude and less rapidly for lower detected amplitude. The application 122 may command a speaker of the device 104 to output an audible alert 134 when a voltage or an electromagnetic field is detected by the module 102. The application 122 may command a vibrator mechanism of the device 104 to vibrate 136 the device 104 when a voltage or an electromagnetic field is detected by the module 102.

Figure 2:
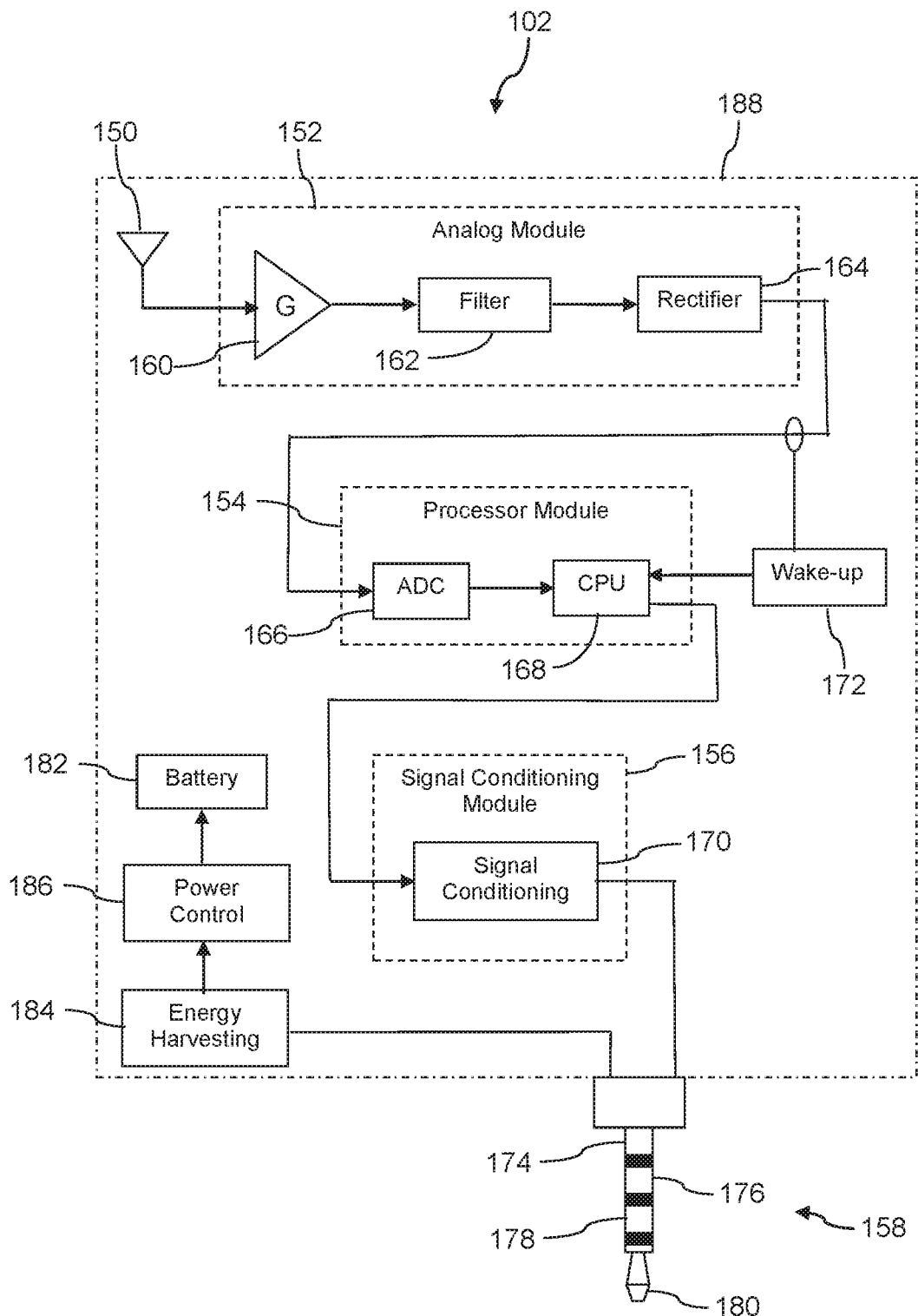
FIG. 2 is a block diagram of a non-contact voltage detector module according to an embodiment of the disclosure.

Turning now to FIG. 2, an embodiment of the non-contact voltage detector module 102 is described. In an embodiment, the module 102 comprises an antenna 150, an analog module 152, a processor module 154, a signal conditioning module 156, and a connector 158. In some contexts, the analog module 152, the processor module 154, and the signal conditioning module 156 may be referred to as an assembly or as a detector assembly. In an embodiment, the assembly or detector assembly may not comprise the signal conditioning module 156. The antenna 150 and the assembly may be enclosed by a package or housing 188, for example a rugged plastic lozenge. It is appreciated that the module 102 may be implemented in a variety of different structures. For example, portions of the module 102 (the assembly) may be implemented as an application specific integrated circuit (ASIC) or as a system on a chip (SOC). The module 102 may be implemented as a circuit board with multiple electronic components coupled to each other by metal traces on or in the circuit board.

In an embodiment, the analog module 152 comprises an amplifier 160, a filter 162, and a rectifier 164. The amplifier 160 is an analog component and boosts the strength of the electromagnetic energy received by the antenna 150 from the electromagnetic field 108. The amplifier 160 may have an automatic gain adjust to adapt the amplifier gain based on the strength of the electromagnetic field 108. For example, the strength or amplitude of the electromagnetic field 108 may be different depending on whether the voltage in the lines 106 is 110 VAC, 220 VAC, 1000 VAC, or some higher voltage. The automatic gain control may not adapt the gain of the amplifier 160 when the electromagnetic energy received by the antenna 150 is below a threshold energy level. The automatic gain adjust may be an analog circuit component.

The output of the amplifier 160 feeds the input of the filter 162. The filter 162 is a frequency selective analog component that transmits or passes unattenuated allowed frequency components and attenuates non-allowed frequency components. In an embodiment, the filter 162 is a bandpass filter that passes unattenuated the frequency components of its input that lie within the frequency of the pass band defined for the filter 162 and attenuates the amplitude of the frequency components of its input that lie outside the pass band of the filter 162, frequency components at both a higher frequency than the high threshold of the pass band and frequency components at a lower frequency that the low threshold of the pass band. For example, the frequency component of the input that is outside the passband of the filter 162 is attenuated by at least 3 dB (−3 dB is the half power threshold, −6 dB is quarter power threshold, −9 dB is the eighth power threshold).

In an embodiment, the pass band of the filter 162 is from about 50 Hz to about 60 Hz. 50 Hz and 60 Hz correspond to commonly available commercial electrical power frequency. For example, 60 Hz commercial electrical power is common in the United States, Canada, Mexico, and parts of South America while 50 Hz commercial electrical power is common in Europe, Russia, China, India, Australia, and most of Africa. Alternatively, the pass band of the filter 162 may be from about 45 Hz to about 65 Hz. Alternatively, for modules 102 designed for use in 50 Hz power systems, the pass band of the filter 162 may be from about 45 Hz to about 55 Hz, and for modules 102 designed for use in 60 Hz power systems, the pass band of the filter 162 may be from about 55 Hz to about 65 Hz. The bandpass filtering on the output of the amplifier 160 promotes rejecting electromagnetic energy or signal that may not be relevant to evaluating whether the lines 106 are energized or not.

Alternatively, in an embodiment, the filter 162 is a low pass filter whose pass band extends from 0 Hz (e.g., DC) to about 60 Hz or to about 65 Hz. In an embodiment of the module 102 targeted for use in a region serviced by 50 Hz electrical power, the low pass filter pass band may extend from 0 Hz to about 50 Hz or to about 55 Hz.

The output of the filter 162 feeds the input of the rectifier 164. The signal received by the antenna 150 and fed through the amplifier 160 and the filter 162 is an alternating current (AC) signal, e.g., a signal having both negative voltage components and positive voltage components. The rectifier 164 converts this AC signal to a DC signal: a signal that has only positive voltage components or only negative voltage components. The rectifier 164 may be implemented in a variety of ways. The rectifier may comprise one or more diodes. The rectifier may provide full-wave rectification, may provide half-wave rectification, or some other kind of rectification.

The output of the rectifier 164 and of the analog module 152 feeds the input of the processor module 154 and the input of the analog to digital converter 166. The analog to digital converter 166 converts the input to a digital value representing the analog input. The analog to digital converter 166 may produce a sequence of digital values, for example a different digital value for each sample time interval. The output of the analog to digital converter 166 is input to a processor 168, for example a microcontroller or some other electronic logic component. The processor 168 converts its input into a pulse wave output, the frequency of which is determined based on the value of the digital value input to the processor 168. In an embodiment, when a low digital value (e.g., an approximately zero digital value) is input, the processor 168 outputs an about 1,000 Hz pulse wave output or an about 800 Hz pulse wave output, when a high digital value (e.g., an approximately maximum digital value for the bit length of the digital value representation) is input, the processor 168 outputs an about 4,000 Hz pulse wave output. In an embodiment, when a digital value is input that is below a low threshold value, the processor 168 outputs an about 1,000 Hz pulse wave output or an about 800 Hz pulse wave output. As the digital value ranges from the minimum digital value to the maximum digital value, the frequency of the pulse wave output varies from about 1,000 Hz to about 4,000 Hz, assuming intermediate frequency values for intermediate digital input values. In an embodiment, the pulse wave output frequency ranges from about 800 Hz to about 4,200 Hz. In an embodiment, the pulse wave output by the processor 168 is a DC signal. In an embodiment, the voltage of the pulse wave output by the processor 168 varies between 0 volts and a positive voltage (e.g., never goes distinctly negative in value) or the pulse wave output by the processor 168 varies between 0 volts and a negative voltage (e.g., never goes distinctly positive in value).

The restriction of the frequency of the output of the processor 168 corresponds to a frequency range consistent with the frequency range of the human voice. The frequency range of the human voice extends from about 300 Hz to about 4,200 Hz. This restricted frequency range is suitable for use in driving a microphone input of the mobile communication device 104. The low frequency limit of the pulse wave output, 1,000 Hz, is somewhat higher than the low frequency limit of the human voice, but this frequency is more easily processed by the non-contact voltage detection application 122 executing on the mobile communication device 104 than lower frequencies may be. Additionally, 4,000 Hz is readily processed by the non-contact voltage detection application 122.

In an embodiment, the processor 168 determines a frequency of the input, for example a frequency that comports with the frequency of the electrical power carried in the lines 106. The electrical power carried in the lines 106 and/or the lines 106 themselves may be referred to in some contexts as electrical power mains. The processor 168 may generate the pulse wave output so as to provide an indication of the frequency of the electrical power. In an embodiment, the peak value of the pulse wave output may be a first value when a 50 Hz electrical power frequency is determined and may be a second value when a 60 Hz electrical power frequency is determined. In another embodiment, the pulse wave output may be interrupted for predefined durations of time when a first electrical power frequency is determined and may be uninterrupted when a second electrical power frequency is determined. For example, in an embodiment, if 50 Hz electrical power frequency is detected, the processor 168 may interrupt the pulse wave output for 1/10 second one time per second or in some other pattern. The non-contact voltage detection application 122 executing on the mobile communication device 104 observes the pattern of interruptions (or no pattern of interruptions) and determines the electrical power frequency accordingly.

In an embodiment, the non-contact voltage detector module 102 comprises a wake-up circuit 172. The wake-up circuit 172 may turn off the processor module 154 or the processor 168 when no electromagnetic energy or signal is received by the antenna 150. The wake-up circuit may monitor the rectified input to the processor module 154 and trigger the processor module 154 and/or processor 168 to reawaken when dormant and to resume processing when the rectified input amplitude exceeds a predefined threshold. The wake-up circuit 172 may be configured to wait a predetermined time duration with no electromagnetic energy received by the antenna 150 before shutting down the processor module 154 or the processor 168. In an embodiment, the processor module 154 or the processor 168 may be the most significant consumers of electrical power in the non-contact voltage detector module 154.

The output of the processor 168 and of the processor module 154 feeds the input of the signal conditioning module 156 and the signal conditioning component 170. The signal conditioning component 170 changes the DC pulse wave output into an AC signal that has a first harmonic frequency that is the same as the frequency of the pulse wave output of the processor module 154. The signal conditioning component 170 may be said to filter and/or to smooth the pulse wave output of the processor module 154. This filtering may band pass filter the DC pulse wave output to remove the DC component and to attenuate high frequency AC components (e.g, frequencies above 40,000 Hz, frequencies above 20,000 Hz, frequencies above 10,000 Hz, or some other frequency threshold. As described above, a frequency limit of the bandpass may be defined by the point where the filter or signal conditioning component 170 attenuates the amplitude of a signal at the subject frequency by 3 dB. In an embodiment, the filtering may only filter out the DC component of the pulse wave, leaving the higher frequency components of the DC pulse wave substantially unattenuated (i.e., attenuated less than 3 dB).

It is understood by those skilled in the art of electrical or electronic communications that a DC pulse wave signal, such as that output by the processor 168 and the processor module 154, may be conceptualized to be a sum of a DC voltage and a series of AC sinusoidal signals that are called harmonics. The first harmonic or fundamental is a sinusoid of the same frequency as the DC pulse wave (i.e., the frequency of a repeating pattern of the pulse). The other harmonics that comprise such a DC pulse wave each has a frequency that is an odd integer multiple of the first harmonic: the third harmonic (with a frequency 3 times the frequency of the frequency of the first harmonic), the fifth harmonic (with a frequency 5 times the frequency of the first harmonic), the seventh harmonic (with a frequency 7 times the frequency of the first harmonic), etc. Typically the first harmonic has the highest amplitude of the harmonics and typically each successive odd multiple harmonic is of lower amplitude than the previous odd multiple harmonic. It will be appreciated that a real-world DC pulse signal is not an ideal wave form and hence the spectral and/or frequency content of such a non-ideal wave departs somewhat from this idealized analysis.

The first harmonic of the AC signal output by the signal conditioning module 156 and hence of the non-contact voltage detector module 102 may be said to be restricted to the frequency range established by the processor module 154 and/or the processor 168. In an embodiment, the first harmonic of the AC signal output by the signal conditioning module 156 may be restricted to the frequency range of the human voice (e.g., from about 300 Hz to about 4,200 Hz). In an embodiment, the first harmonic of the AC signal output by the signal conditioning module 156 may be restricted to the frequency range of about 800 Hz to about 4,200 Hz. In an embodiment, the first harmonic of the AC signal output by the signal conditioning module 156 may be restricted to the frequency range of about 1,000 Hz to about 4,000 Hz.

In an embodiment, the non-contact voltage detector module 102 does not comprise a signal conditioning component 170 or the signal conditioning module 156. For example, the DC pulse wave output from the processor module 154 may be output directly to the connector 158. It may be that the input connector of the mobile communication device 104 provides bandpass filtering, and hence it may be superfluous to perform filtering by the signal conditioning module 156. Alternatively, it may be that it is in the nature of the electrical connection between the connector 158 and the connector of the mobile communication device 104 that the connection acts as a low pass filter, attenuating high frequency components of the DC pulse wave output of the processor module 154. Finally, it may be that in some circumstances the presence of high frequency components in the signal input to the mobile communication device 104 does no harm and does not interfere with analyzing the content of the input signal to identify and take action based on the first harmonic in the signal. Thus, it is contemplated that some implementations of the non-contact voltage detector modules 102 may have the signal conditioning module 156 while other implementations of the non-contact voltage detector modules 102 may not have the signal conditioning module 156. This may promote a manufacturer offering functionally similar products of different quality levels having different price points. For example, the manufacturer may provide a higher quality module 102 that has the signal conditioning module 156 that is sold at a higher price and may provide a lower quality module 102 without the signal conditioning module 156 that is sold at a lower price.

The output of the signal conditioning module 156 or the processor module 154 feeds the connector 158. In an embodiment, the connector 158 is a 3.5 mm TRRS (tip-ring-ring-sleeve) connector or jack, but it is understood that the teachings of the present disclosure are consistent with using other connection structures and mechanisms. The connector 158 may comprise a sleeve 174, a first ring 176, a second ring 178, and a tip 180. In an embodiment, the output of the signal conditioning module 156 feeds the sleeve 174 of the connector 158. The sleeve 174 may correspond to a microphone input contact in a connector and/or receptacle of the mobile communication device 104.

The connector 158 may be inserted into a connector or receptacle of the mobile communication device 104, as shown in FIG. 1. The non-contact voltage detection application 122 may monitor the signal output by the signal conditioning module 156 or the signal output by the processor module 154, for example using a device driver interface provided by the mobile communication device 104 and/or an operating system executing on the device 104. The non-contact voltage detection application 122 can analyze the signal and determine a strength of the electromagnetic field 108 sensed by the antenna 150 and present a corresponding indication on the display 120 as described above. For example, the non-contact voltage detection application 122 may perform a spectral analysis or a frequency analysis of the signal output by the signal conditioning module 156 or the processor module 154. This may be performed, in part, using digital signal processing algorithms on a sequence of digital values that are derived from sampling and analog-to-digital converting the input to the device 104. Based on the spectral analysis, the application 122 may identify the first harmonic or fundamental harmonic of the input, and based on the frequency of the first harmonic or fundamental harmonic determine whether the lines 106 are energized or not energized.

In an embodiment, the non-contact voltage detection application 122 may create a log of the events experienced by the mobile communication device 104, for example the events of detections of electrical power activation associated with a time of the event and a self-location position (e.g., a pair of GPS coordinates, trilateration position developed from proximate cell towers, the like). This log may be assembled over time and periodically pushed to a sever computer via a wireless communication link, for example to a cell tower according to one or more of long term evolution (LTE), code division multiple access (CDMA), global system for mobile communication (GSM), worldwide interoperability for microwave access (WiMAX), WiFi, Bluetooth, or some other wireless communication protocol. The log may then be transmitted to a server computer and/or data base management system (DBMS) for archival or long term storage. The log, collected with that of other employees of an enterprise or business, may be used to audit the safety compliance of an enterprise or business.

The non-contact voltage detector module 102 may further comprise a battery 182 that provides power to the module 102. In an embodiment, the battery 182 may be removable and replaceable. For example, the battery 182 may be a 3 volt coin-shaped battery. Alternatively, the battery 182 may be a rechargeable battery. The module 102 may further comprise an energy harvesting component 184 and a power control component 186. The energy harvesting component 184 may receive power from the second ring 178 or from the tip 180 of the connector 158. In an embodiment, the mobile communication device 104 may output an audio frequency signal (e.g., 15,000 Hz to 20,000 Hz), under control of the application 122, via a speaker contact in the connector or receptacle of the mobile communication device 104, and this signal may be fed from the connector 158 to the energy harvesting component 184. The energy harvesting component 184 may convert this audio signal into an electrical energy resource and output this electrical power to the power control component 186. The power control component 186 may mediate recharging the battery 182 and/or powering the modules 152, 154, and 156. In some contexts, the energy harvesting component 184 may be said to provide power to the analog module 152, the processing module 154, and the signal conditioning module 156, for example via the power control component 186 and/or via the battery 182.

It is understood that the components of the non-contact voltage detector module 102 may be implemented in a different way. For example, the output of the amplifier 160 may be converted from an analog value to a digital value, and all the processing ascribed above to the filter 162, the rectifier 164, the analog to digital converter 166, the processor 168 may be performed by software executing on a processor in the module 102. For example, an initial digital value output by the amplifier 160 may be digitally filtered, that digitally filtered signal analyzed to convert the filtered signal to a pulse wave frequency signal and output to be filtered or smoothed by the signal conditioning module 158. In an embodiment, the module 102 may be said to convert the electromagnetic signal received by the antenna 150 to the pulse wave frequency signal output to the connector 158.

Figure 3:
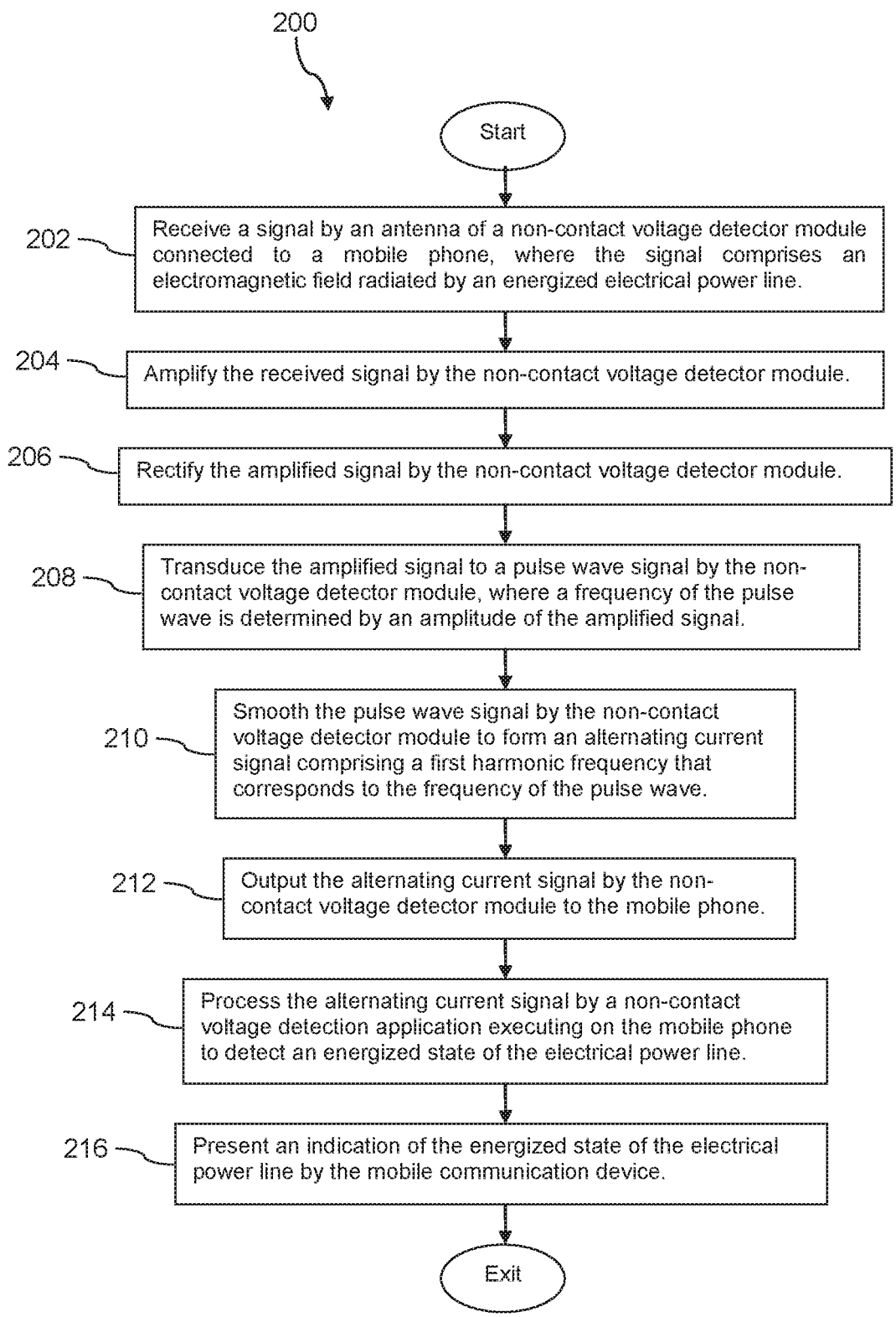
FIG. 3 is a flow chart of a method according to an embodiment of the disclosure.

Turning now to FIG. 3, a method 200 is described. At block 202, receive a signal by an antenna of a non-contact voltage detector module connected to a mobile phone, where the signal comprises an electromagnetic field radiated by an energized electrical power line. At block 204, amplify the received signal by the non-contact voltage detector module. At block 206, rectify the amplified signal by the non-contact voltage detector module. In an embodiment, the amplified signal may be filtered before it is rectified, for example low pass filtered or bandpass filtered. At block 208, convert the amplified signal to a pulse wave signal by the non-contact voltage detector module, where a frequency of the pulse wave is determined by an amplitude of the amplified signal. At block 210, smooth and/or filter the pulse wave signal by the non-contact voltage detector module to form an alternating current signal comprising a first harmonic frequency that corresponds to the frequency of the pulse wave. The filtering of block 210 may be said to remove or block a direct current (DC) component of the pulse wave signal output. At block 212, output the alternating current signal by the non-contact voltage detector module to the mobile phone. At block 214, process the alternating current signal by a non-contact voltage detection application executing on the mobile phone to detect an energized state of the electrical power line. At block 216, present an indication of the energized state of the electrical power line by the mobile communication device.

Figure 4:
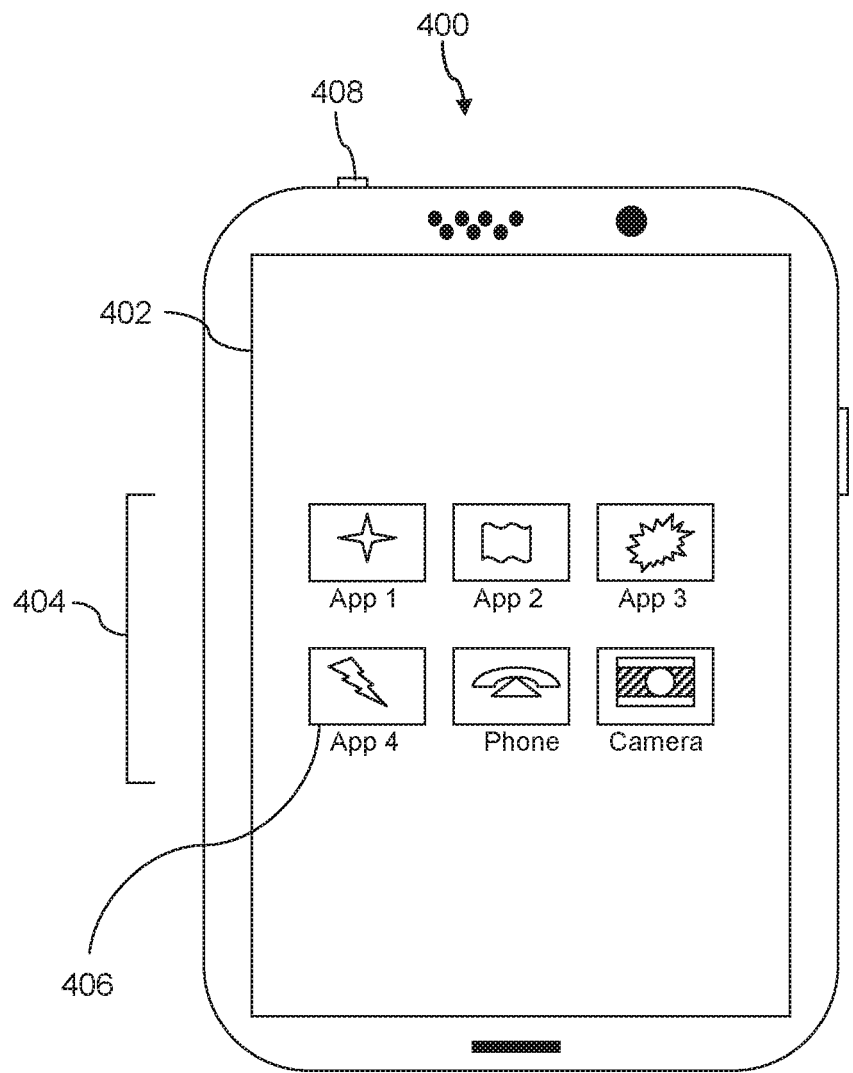
FIG. 4 is an illustration of a mobile communication device according to an embodiment of the disclosure.

FIG. 4 depicts a mobile communication device 400, which is operable for implementing aspects of the present disclosure, but the present disclosure should not be limited to these implementations. For example, the mobile communication device 104 may be substantially similar to device 400. Though illustrated as a mobile phone, the mobile communication device 400 may take various forms including a wireless handset, a pager, a personal digital assistant (PDA), a gaming device, or a media player. The mobile communication device 400 includes a touchscreen display 402 having a touch-sensitive surface for input by a user. A small number of application icons 404 are illustrated within the touch screen display 402. An icon 406 that may be touched to launch the non-contact voltage detection application 122 may be among the icons 404. It is understood that in different embodiments, any number of application icons 404 may be presented in the touch screen display 402. In some embodiments of the mobile communication device 400, a user may be able to download and install additional applications on the mobile communication device 400, and an icon associated with such downloaded and installed applications may be added to the touch screen display 402 or to an alternative screen. The mobile communication device 400 may comprise other components such as electromechanical switches, speakers, camera lenses, microphones, input and/or output connectors, and other components as are well known in the art. For example, in an embodiment, the mobile communication device 400 comprises a connector 408 or a receptacle that is configured to receive a jack such as the connector 158.

The mobile communication device 400 may present options for the user to select, controls for the user to actuate, and/or cursors or other indicators for the user to direct. The mobile communication device 400 may further accept data entry from the user, including numbers to dial or various parameter values for configuring the operation of the handset. The mobile communication device 400 may further execute one or more software or firmware applications in response to user commands. These applications may configure the mobile communication device 400 to perform various customized functions in response to user interaction. Additionally, the mobile communication device 400 may be programmed and/or configured over-the-air, for example from a wireless base station, a wireless access point, or a peer mobile communication device 400. The mobile communication device 400 may execute a web browser application which enables the touch screen display 402 to show a web page. The web page may be obtained via wireless communications with a base transceiver station, a wireless network access node, a peer mobile communication device 400 or any other wireless communication network or system.

Figure 5:
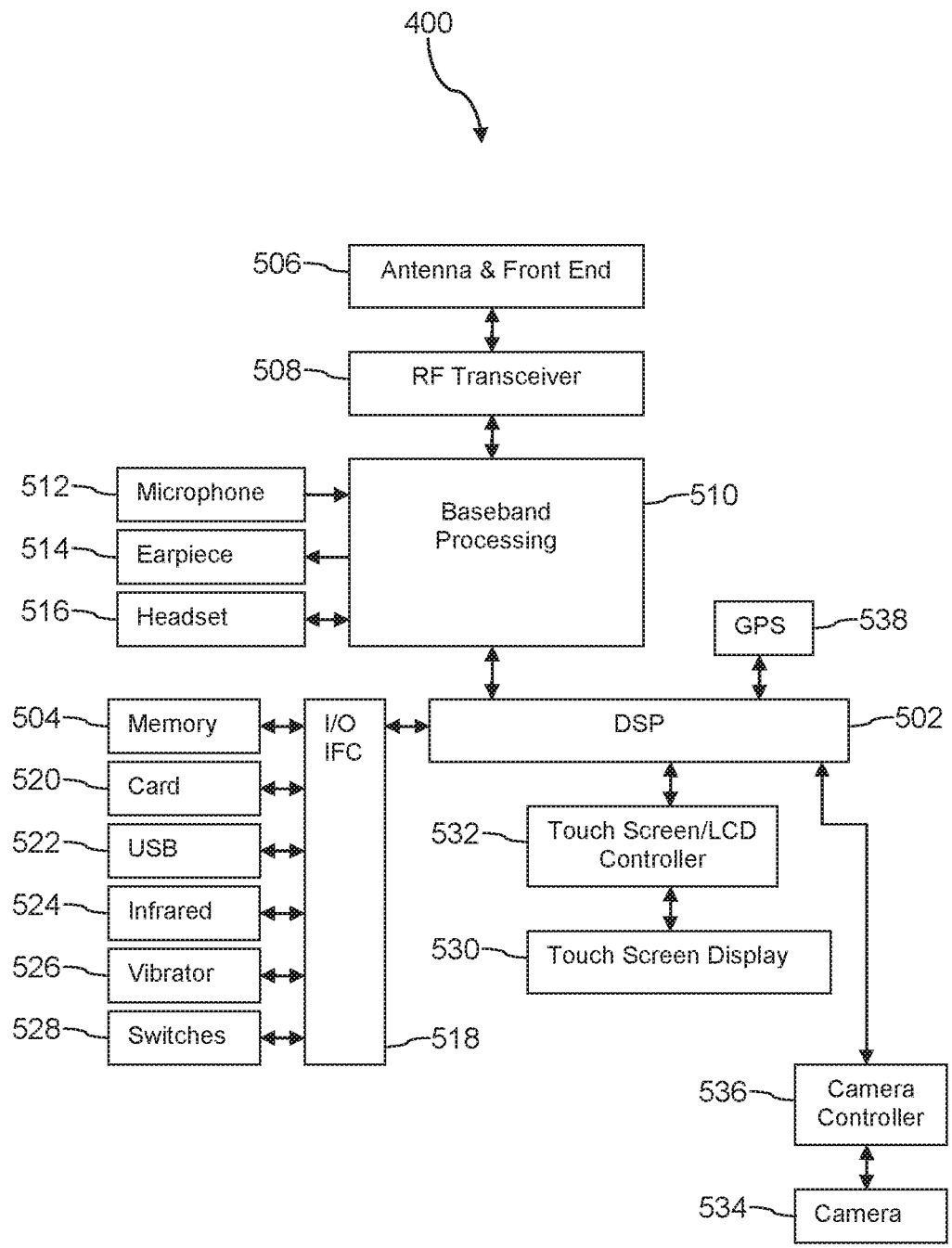
FIG. 5 is a block diagram of a hardware architecture of a mobile communication device according to an embodiment of the disclosure.

FIG. 5 shows a block diagram of the mobile communication device 400. While a variety of known components of handsets are depicted, in an embodiment a subset of the listed components and/or additional components not listed may be included in the mobile communication device 400. The mobile communication device 400 includes a digital signal processor (DSP) 502 and a memory 504. As shown, the mobile communication device 400 may further include an antenna and front end unit 506, a radio frequency (RF) transceiver 508, a baseband processing unit 510, a microphone 512, an earpiece speaker 514, a headset port 516, an input/output interface 518, a removable memory card 520, a universal serial bus (USB) port 522, an infrared port 524, a vibrator 526, one or more electro-mechanical switches 528, a touch screen liquid crystal display (LCD) with a touch screen display 530, a touch screen/LCD controller 532, a camera 534, a camera controller 536, and a global positioning system (GPS) receiver 538. In an embodiment, the mobile communication device 400 may include another kind of display that does not provide a touch sensitive screen. In an embodiment, the mobile communication device 400 may include both the touch screen display 530 and additional display component that does not provide a touch sensitive screen. In an embodiment, the DSP 502 may communicate directly with the memory 504 without passing through the input/output interface 518. Additionally, in an embodiment, the mobile communication device 400 may comprise other peripheral devices that provide other functionality.

The DSP 502 or some other form of controller or central processing unit operates to control the various components of the mobile communication device 400 in accordance with embedded software or firmware stored in memory 504 or stored in memory contained within the DSP 502 itself. In addition to the embedded software or firmware, the DSP 502 may execute other applications stored in the memory 504 or made available via information carrier media such as portable data storage media like the removable memory card 520 or via wired or wireless network communications. The application software may comprise a compiled set of machine-readable instructions that configure the DSP 502 to provide the desired functionality, or the application software may be high-level software instructions to be processed by an interpreter or compiler to indirectly configure the DSP 502.

The DSP 502 may communicate with a wireless network via the analog baseband processing unit 510. In some embodiments, the communication may provide Internet connectivity, enabling a user to gain access to content on the Internet and to send and receive e-mail or text messages. The input/output interface 518 interconnects the DSP 502 and various memories and interfaces. The memory 504 and the removable memory card 520 may provide software and data to configure the operation of the DSP 502. Among the interfaces may be the USB port 522 and the infrared port 524. The USB port 522 may enable the mobile communication device 400 to function as a peripheral device to exchange information with a personal computer or other computer system. The infrared port 524 and other optional ports such as a Bluetooth interface or an IEEE 802.11 compliant wireless interface may enable the mobile communication device 400 to communicate wirelessly with other nearby handsets and/or wireless base stations. In an embodiment, the mobile communication device 400 may comprise a near field communication (NFC) transceiver. The NFC transceiver may be used to complete payment transactions with point-of-sale terminals or other communications exchanges. In an embodiment, the mobile communication device 400 may comprise a radio frequency identify (RFID) reader and/or writer device.

The switches 528 may couple to the DSP 502 via the input/output interface 518 to provide one mechanism for the user to provide input to the mobile communication device 400. Alternatively, one or more of the switches 528 may be coupled to a motherboard of the mobile communication device 400 and/or to components of the mobile communication device 400 via a different path (e.g., not via the input/output interface 518), for example coupled to a power control circuit (power button) of the mobile communication device 400. The touch screen display 530 is another input mechanism, which further displays text and/or graphics to the user. The touch screen LCD controller 532 couples the DSP 502 to the touch screen display 530. The GPS receiver 538 is coupled to the DSP 502 to decode global positioning system signals, thereby enabling the mobile communication device 400 to determine its position.

Figure 6A:
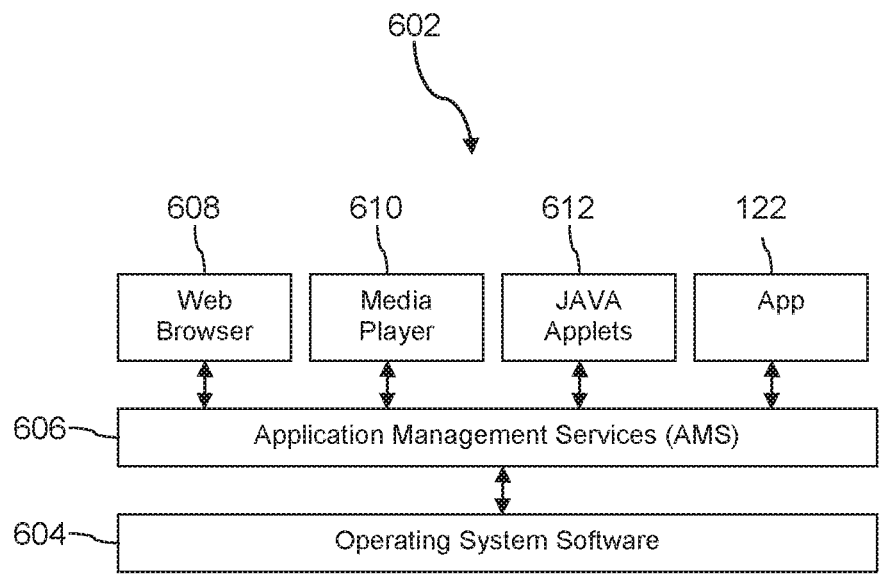
FIG. 6A is a block diagram of a software architecture of a mobile communication device according to an embodiment of the disclosure.

FIG. 6A illustrates a software environment 602 that may be implemented by the DSP 502. The DSP 502 executes operating system software 604 that provides a platform from which the rest of the software operates. The operating system software 604 may provide a variety of drivers for the handset hardware with standardized interfaces that are accessible to application software. The operating system software 604 may be coupled to and interact with application management services (AMS) 606 that transfer control between applications running on the mobile communication device 400. Also shown in FIG. 6A are a web browser application 608, a media player application 610, and JAVA applets 612. The web browser application 608 may be executed by the mobile communication device 400 to browse content and/or the Internet, for example when the mobile communication device 400 is coupled to a network via a wireless link. The web browser application 608 may permit a user to enter information into forms and select links to retrieve and view web pages. The media player application 610 may be executed by the mobile communication device 400 to play audio or audiovisual media. The JAVA applets 612 may be executed by the mobile communication device 400 to provide a variety of functionality including games, utilities, and other functionality. The non-contact voltage detection application 122 may likewise execute as an application in the context of or calling upon the application management services 606.

Figure 6B:
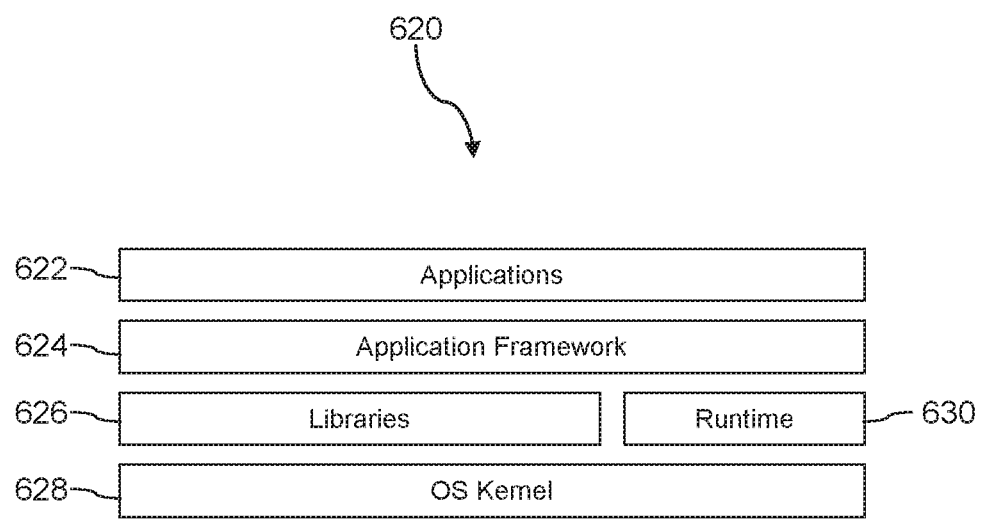
FIG. 6B is a block diagram of another software architecture of a mobile communication device according to an embodiment of the disclosure.

FIG. 6B illustrates an alternative software environment 620 that may be implemented by the DSP 502. The DSP 502 executes operating system kernel (OS kernel) 628 and an execution runtime 630. The DSP 502 executes applications 622 that may execute in the execution runtime 630 and may rely upon services provided by the application framework 624. Applications 622 and the application framework 624 may rely upon functionality provided via the libraries 626. In an embodiment, the non-contact voltage detection application 122 may be considered to be one of the applications 622.

Figure 7:
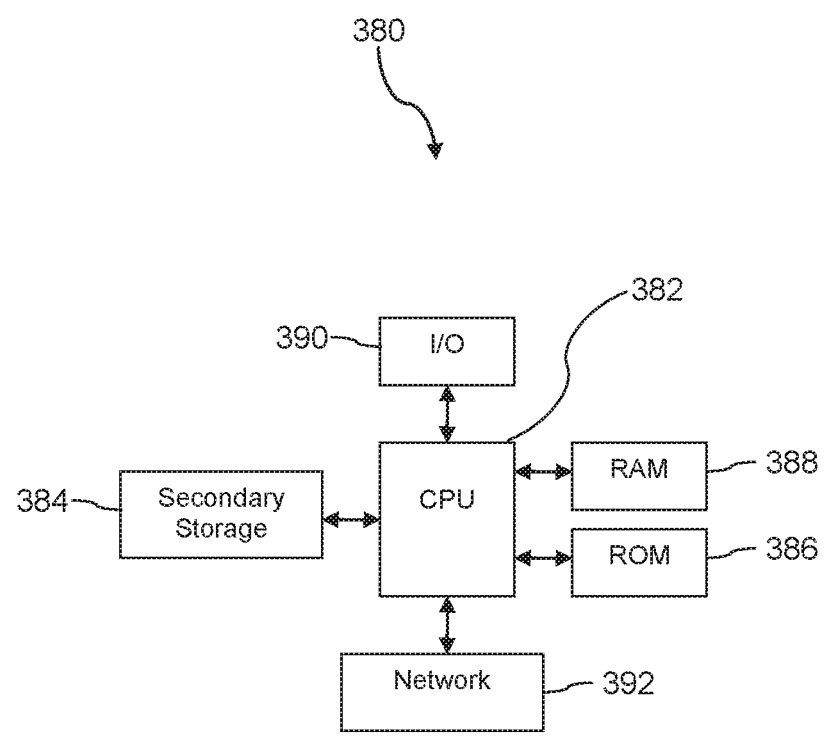
FIG. 7 is a block diagram of a computer system according to an embodiment of the disclosure.

FIG. 7 illustrates a computer system 380 suitable for implementing one or more embodiments disclosed herein. The server computer and/or DBMS that receives logs of electrical power detection events discussed above with reference to FIG. 2 may be implemented as a computer system 380. The computer system 380 includes a processor 382 (which may be referred to as a central processor unit or CPU) that is in communication with memory devices including secondary storage 384, read only memory (ROM) 386, random access memory (RAM) 388, input/output (I/O) devices 390, and network connectivity devices 392. The processor 382 may be implemented as one or more CPU chips.

It is understood that by programming and/or loading executable instructions onto the computer system 380, at least one of the CPU 382, the RAM 388, and the ROM 386 are changed, transforming the computer system 380 in part into a particular machine or apparatus having the novel functionality taught by the present disclosure. It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

Additionally, after the system 380 is turned on or booted, the CPU 382 may execute a computer program or application. For example, the CPU 382 may execute software or firmware stored in the ROM 386 or stored in the RAM 388. In some cases, on boot and/or when the application is initiated, the CPU 382 may copy the application or portions of the application from the secondary storage 384 to the RAM 388 or to memory space within the CPU 382 itself, and the CPU 382 may then execute instructions that the application is comprised of. In some cases, the CPU 382 may copy the application or portions of the application from memory accessed via the network connectivity devices 392 or via the I/O devices 390 to the RAM 388 or to memory space within the CPU 382, and the CPU 382 may then execute instructions that the application is comprised of. During execution, an application may load instructions into the CPU 382, for example load some of the instructions of the application into a cache of the CPU 382. In some contexts, an application that is executed may be said to configure the CPU 382 to do something, e.g., to configure the CPU 382 to perform the function or functions promoted by the subject application. When the CPU 382 is configured in this way by the application, the CPU 382 becomes a specific purpose computer or a specific purpose machine.

The secondary storage 384 is typically comprised of one or more disk drives or tape drives and is used for non-volatile storage of data and as an over-flow data storage device if RAM 388 is not large enough to hold all working data. Secondary storage 384 may be used to store programs which are loaded into RAM 388 when such programs are selected for execution. The ROM 386 is used to store instructions and perhaps data which are read during program execution. ROM 386 is a non-volatile memory device which typically has a small memory capacity relative to the larger memory capacity of secondary storage 384. The RAM 388 is used to store volatile data and perhaps to store instructions. Access to both ROM 386 and RAM 388 is typically faster than to secondary storage 384. The secondary storage 384, the RAM 388, and/or the ROM 386 may be referred to in some contexts as computer readable storage media and/or non-transitory computer readable media.

I/O devices 390 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 392 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards that promote radio communications using protocols such as code division multiple access (CDMA), global system for mobile communications (GSM), long-term evolution (LTE), worldwide interoperability for microwave access (WiMAX), near field communications (NFC), radio frequency identity (RFID), and/or other air interface protocol radio transceiver cards, and other well-known network devices. These network connectivity devices 392 may enable the processor 382 to communicate with the Internet or one or more intranets. With such a network connection, it is contemplated that the processor 382 might receive information from the network, or might output information to the network in the course of performing the above-described method steps. Such information, which is often represented as a sequence of instructions to be executed using processor 382, may be received from and outputted to the network, for example, in the form of a computer data signal embodied in a carrier wave.

Such information, which may include data or instructions to be executed using processor 382 for example, may be received from and outputted to the network, for example, in the form of a computer data baseband signal or signal embodied in a carrier wave. The baseband signal or signal embedded in the carrier wave, or other types of signals currently used or hereafter developed, may be generated according to several methods well-known to one skilled in the art. The baseband signal and/or signal embedded in the carrier wave may be referred to in some contexts as a transitory signal.

The processor 382 executes instructions, codes, computer programs, scripts which it accesses from hard disk, floppy disk, optical disk (these various disk based systems may all be considered secondary storage 384), flash drive, ROM 386, RAM 388, or the network connectivity devices 392. While only one processor 382 is shown, multiple processors may be present. Thus, while instructions may be discussed as executed by a processor, the instructions may be executed simultaneously, serially, or otherwise executed by one or multiple processors. Instructions, codes, computer programs, scripts, and/or data that may be accessed from the secondary storage 384, for example, hard drives, floppy disks, optical disks, and/or other device, the ROM 386, and/or the RAM 388 may be referred to in some contexts as non-transitory instructions and/or non-transitory information.

In an embodiment, the computer system 380 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computer system 380 to provide the functionality of a number of servers that is not directly bound to the number of computers in the computer system 380. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In an embodiment, some or all of the functionality disclosed above may be provided as a computer program product. The computer program product may comprise one or more computer readable storage medium having computer usable program code embodied therein to implement the functionality disclosed above. The computer program product may comprise data structures, executable instructions, and other computer usable program code. The computer program product may be embodied in removable computer storage media and/or non-removable computer storage media. The removable computer readable storage medium may comprise, without limitation, a paper tape, a magnetic tape, magnetic disk, an optical disk, a solid state memory chip, for example analog magnetic tape, compact disk read only memory (CD-ROM) disks, floppy disks, jump drives, digital cards, multimedia cards, and others. The computer program product may be suitable for loading, by the computer system 380, at least portions of the contents of the computer program product to the secondary storage 384, to the ROM 386, to the RAM 388, and/or to other non-volatile memory and volatile memory of the computer system 380. The processor 382 may process the executable instructions and/or data structures in part by directly accessing the computer program product, for example by reading from a CD-ROM disk inserted into a disk drive peripheral of the computer system 380. Alternatively, the processor 382 may process the executable instructions and/or data structures by remotely accessing the computer program product, for example by downloading the executable instructions and/or data structures from a remote server through the network connectivity devices 392. The computer program product may comprise instructions that promote the loading and/or copying of data, data structures, files, and/or executable instructions to the secondary storage 384, to the ROM 386, to the RAM 388, and/or to other non-volatile memory and volatile memory of the computer system 380.

In some contexts, the secondary storage 384, the ROM 386, and the RAM 388 may be referred to as a non-transitory computer readable medium or a computer readable storage media. A dynamic RAM embodiment of the RAM 388, likewise, may be referred to as a non-transitory computer readable medium in that while the dynamic RAM receives electrical power and is operated in accordance with its design, for example during a period of time during which the computer system 380 is turned on and operational, the dynamic RAM stores information that is written to it. Similarly, the processor 382 may comprise an internal RAM, an internal ROM, a cache memory, and/or other internal non-transitory storage blocks, sections, or components that may be referred to in some contexts as non-transitory computer readable media or computer readable storage media.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A non-contact voltage detector module pluggable to a mobile communication device, comprising:
   an antenna;
   a first connector configured for connecting to a connector of a mobile communication device; and
   an assembly, coupled to the antenna and the first connector, that converts an electromagnetic field received by the antenna to an indication of a strength of the electromagnetic field and transmits the indication of the strength of the electromagnetic field via the first connector, wherein the assembly further converts the electromagnetic field received by the antenna to an indication of a power mains frequency and transmits the indication of the power mains frequency via the first connector.

2. The non-contact voltage detector module of claim 1, wherein the first connector is a tip-ring-ring-sleeve (TRRS) connector, and the assembly transmits the indication of the strength of the electromagnetic field via a sleeve portion of the TRRS connector.

3. The non-contact voltage detector module of claim 1, wherein the indication of the strength of the electromagnetic field transmitted via the first connector is an alternating current (AC) signal comprising a first harmonic restricted by the assembly to a frequency in a frequency range from about 300 Hz to about 4,200 Hz.

4. The non-contact voltage detector module of claim 3, wherein the first harmonic of the AC signal transmitted via the first connector is restricted to a frequency in the range of about 800 Hz to about 4,200 Hz.

5. The non-contact voltage detector module of claim 4, wherein the non-contact voltage detector is configured to convert an amplified signal to a pulse wave signal.

6. The non-contact voltage detector module of claim 5, wherein a frequency of the pulse wave is determined by an amplitude of the amplified signal and an alternating current signal.

7. A non-contact voltage detector module pluggable to a mobile communication device, comprising:
    an antenna;
    an analog module coupled to the antenna that amplifies an input from the antenna, filters the amplified antenna input, and rectifies the filtered input;
    a processing module coupled to the analog module that converts the rectified input from a time varying analog value to a sequence of digital values and converts the digital values to a pulse signal restricted to a frequency range of a human voice where the frequency of the pulse signal is determined by the processing module based on an amplitude of the digital values;
    a signal conditioning module coupled to the processing module that smooths the pulse signal; and
    a connector coupled to the signal conditioning module that outputs the smoothed pulse signal.

8. The non-contact voltage detector module of claim 7, wherein the analog module is configured to band pass filter the amplified antenna input to pass 50 Hz to 60 Hz signals.

9. The non-contact voltage detector module of claim 7, wherein the processing module restricts the pulse signal to a frequency in the range from about 1,000 Hz to about 4,000 Hz.

10. The non-contact voltage detector module of claim 7, further comprising a battery, wherein the analog module, the processing module, and the signal conditioning module are powered by the battery.

11. The non-contact voltage detector module of claim 7, wherein the connector is a tip-ring-ring-sleeve (TRRS) connector, wherein the smoothed signal is output by a sleeve of the TRRS connector, and further comprising an energy harvesting module that harvests power input from one of a ring of the connector or a tip of the connector, wherein the energy harvesting module provides power to the analog module, the processing module, and the signal conditioning module.

12. The non-contact voltage detector module of claim 7, further comprising a wake-up circuit that monitors the rectified input and triggers the processor module to reawaken when dormant and to resume processing when an amplitude of the rectified input exceeds a predefined threshold.

13. The non-contact voltage detector module of claim 7, wherein the processing module further determines a frequency of the rectified input and outputs via the connector an indication of the rectified input frequency as one of 50 Hz or 60 Hz.

14. A method of determining that an electrical power line is energized, comprising:
    receiving a signal by an antenna of a non-contact voltage detector module connected to a mobile phone, where the signal comprises an electromagnetic field radiated by an energized electrical power line;
    amplifying the received signal by the non-contact voltage detector module;
    rectifying the amplified signal by the non-contact voltage detector module;
    converting the amplified signal to a pulse wave signal by the non-contact voltage detector module, where a frequency of the pulse wave is determined by an amplitude of the amplified signal;
    smoothing the pulse wave signal by the non-contact voltage detector module to form an alternating current signal comprising a first harmonic frequency that corresponds to the frequency of the pulse wave;
    outputting the alternating current signal by the non-contact voltage detector module to the mobile phone;
    processing the alternating current signal by a non-contact voltage detection application executing on the mobile phone to detect an energized state of the electrical power line; and
    presenting an indication of the energized state of the electrical power line by the mobile communication device.

15. The method of claim 14, wherein the indication of the energized state comprises a visual indication on a display of the mobile phone.

16. The method of claim 14, wherein the indication of the energized state comprises an aural alert sounded by a speaker of the mobile phone.

17. The method of claim 14, wherein the indication of the energized state comprises a vibration indication provided by a vibrator device of the mobile phone.

18. The method of claim 14, further comprising filtering the amplified signal before rectifying the amplified signal.

19. The method of claim 14, receiving the alternating current signal output by the noncontact voltage detector module by a microphone input contact of the mobile phone.

* * * * *